United States Patent
Kankan et al.

(10) Patent No.: US 8,263,787 B2
(45) Date of Patent: Sep. 11, 2012

(54) PROCESS FOR PREPARING DORZOLAMIDE

(75) Inventors: Rajendra Narayanrao Kankan, Maharashtra (IN); Dharmaraj Ramachandra Rao, Maharashtra (IN); Shrikant Suresh Mudgal, Maharashtra (IN)

(73) Assignee: CIPLA Limited, Mumbai (IN)

( * ) Notice: Subject to any disclaimer, the term of this patent is extended or adjusted under 35 U.S.C. 154(b) by 310 days.

(21) Appl. No.: 12/598,557

(22) PCT Filed: May 7, 2008

(86) PCT No.: PCT/GB2008/001592
§ 371 (c)(1),
(2), (4) Date: Dec. 30, 2009

(87) PCT Pub. No.: WO2008/135770
PCT Pub. Date: Nov. 13, 2008

(65) Prior Publication Data
US 2010/0113804 A1 May 6, 2010

(30) Foreign Application Priority Data
May 7, 2007 (IN) .......................... 866/07

(51) Int. Cl.
*C07D 409/02* (2006.01)
(52) U.S. Cl. ....................................... 549/23
(58) Field of Classification Search ................ 549/23
See application file for complete search history.

(56) References Cited

U.S. PATENT DOCUMENTS

| | | | |
|---|---|---|---|
| 5,157,129 A | 10/1992 | Blacklock et al. | |
| 5,474,919 A | 12/1995 | Chartrain et al. | |
| 5,688,968 A | 11/1997 | Blacklock et al. | |
| 5,760,249 A | 6/1998 | Mathre et al. | |
| 7,109,353 B2 | 9/2006 | Gurjar et al. | |
| 2006/0155132 A1 | 7/2006 | Kovacs et al. | |

FOREIGN PATENT DOCUMENTS

| | | |
|---|---|---|
| EP | 0296879 A1 | 12/1988 |
| WO | 9421645 A1 | 9/1994 |
| WO | 2008135770 A2 | 11/2008 |
| WO | 2008135770 A3 | 11/2008 |

OTHER PUBLICATIONS

Grant, Ed., Hackh's Chemical Dictionary, 4th edition.*
Foreign communication from the priority application—International Search Report and Written Opinion, PCT/GB2008/001592, Mar. 27, 2009, 20 pages.
Foreign communication from the priority application—International Preliminary Report on Patentability, PCT/GB2008/001592, Nov. 19, 2009, 11 pages.

* cited by examiner

*Primary Examiner* — Taofiq A Solola
(74) *Attorney, Agent, or Firm* — Conley Rose, P.C.; Rodney B. Carroll

(57) ABSTRACT

There is provided a process for preparing dorzolamide and processes for preparing intermediates useful in the preparation of dorzolamide. In particular, there is provided a process for preparing an acetoamido sulfone of formula (viii) comprising oxidation of a hydroxysulfonamide of formula (vii) in the presence of an oxidizing agent selected from the group consisting of: a peracid, tert-butyl hydroperoxide, dimethyl dioxirane, selenium dioxide, m-phenanthroline di-N-oxide, nitric acid and hydrogen peroxide. There is also provided a process for preparing an acetoamidosulfone of formula (ix-a) comprising converting a hydroxysulfone of formula (viii) to the acetoamidosulfone of formula (ix-a) in the presence of acetonitrile and an acid. There is also provided a process for separating the cis- and trans-isomers of dorzolamide from a mixture of the trans-isomer of dorzolamide and the cis-isomer of dorzolamide comprising reacting the mixture of isomers with a carboxylic acid.

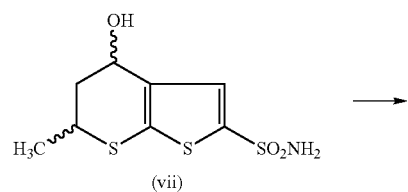

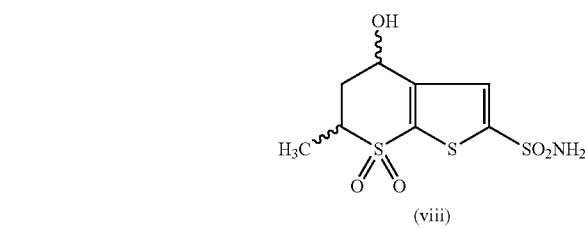

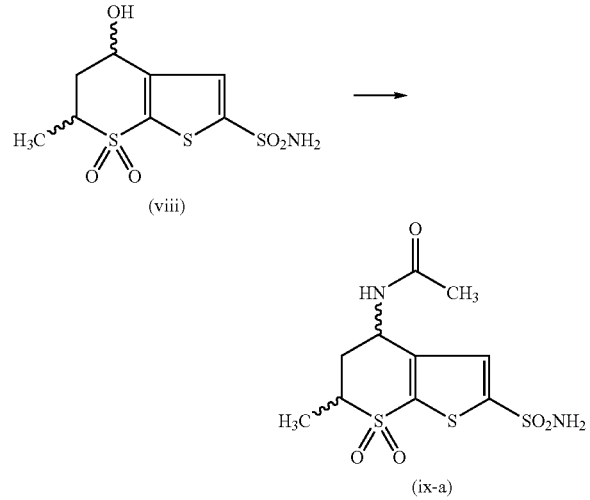

23 Claims, No Drawings

PROCESS FOR PREPARING DORZOLAMIDE

TECHNICAL FIELD OF THE INVENTION

The present invention relates to an improved process for the preparation of dorzolamide hydrochloride.

BACKGROUND OF THE INVENTION

Dorzolamide is chemically termed as (4S,6S)-4-(ethylamino)-5,6-dihydro-6-methyl-4H-thieno[2,3-b]thiopyran-2-sulfonamide 7,7-dioxide hydrochloride. Dorzolamide hydrochloride is represented by following structural Formula I:

Formula I

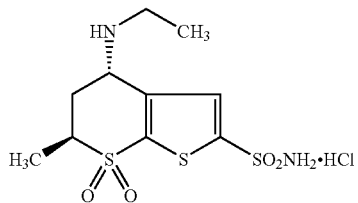

Dorzolamide hydrochloride is known to be a carbonic anhydrase inhibitor useful in the treatment of ocular hypertension.

A process for the preparation of dorzolamide and its derivatives was first described in EP 0296879. The process of particular relevance is depicted in scheme 1.

Scheme 1

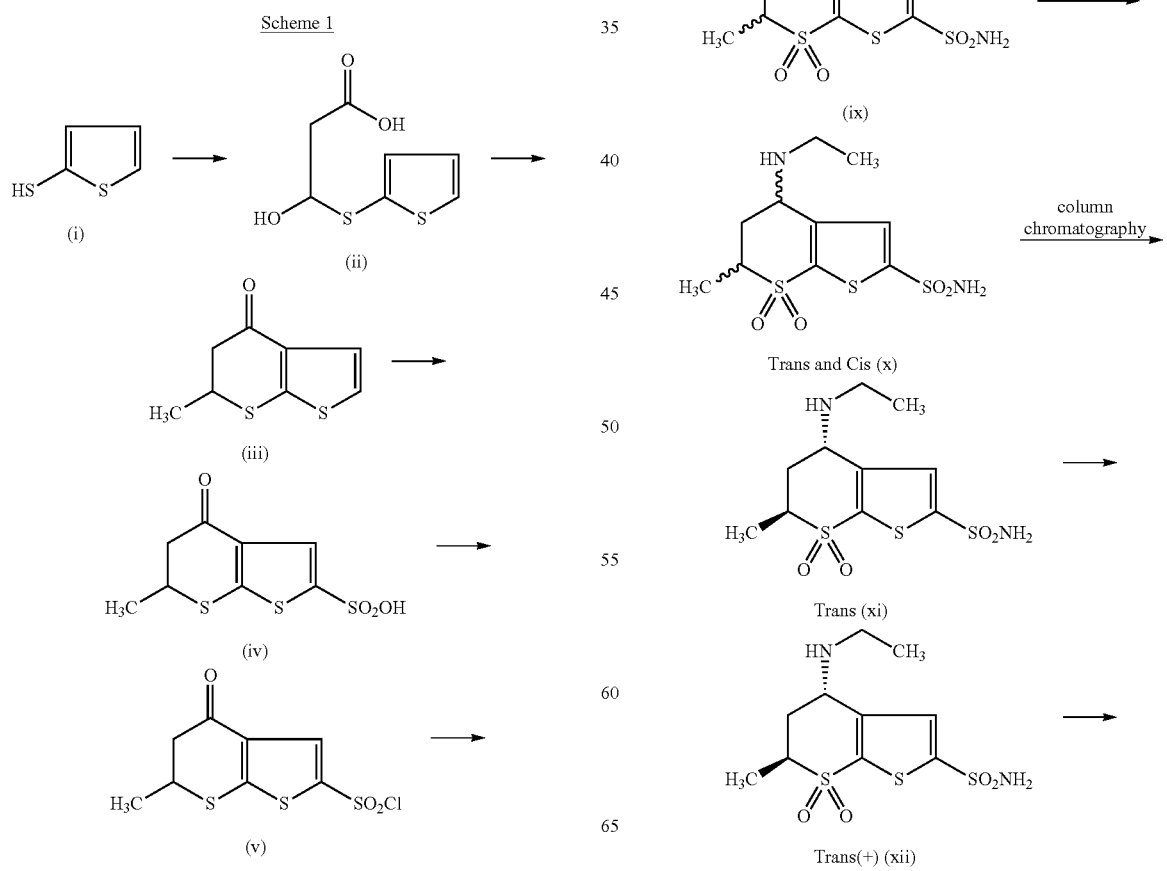

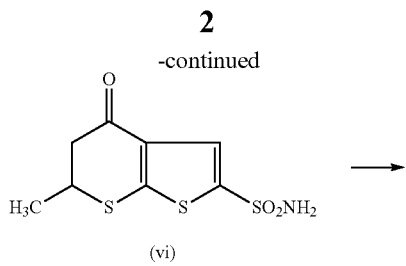

(vi)

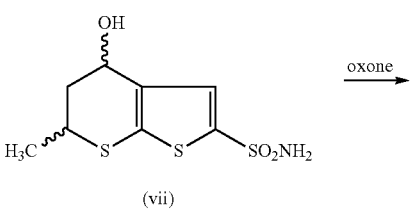

(vii)

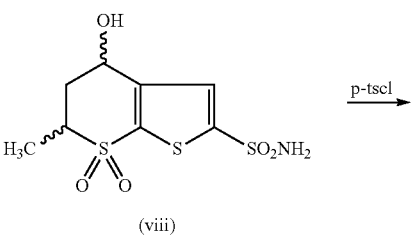

(viii)

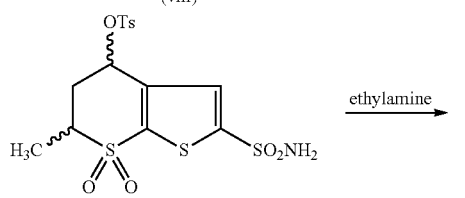

(ix)

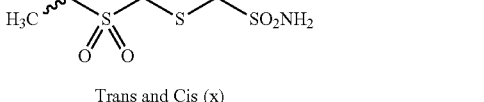

Trans and Cis (x)

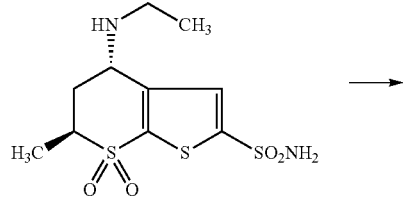

Trans (xi)

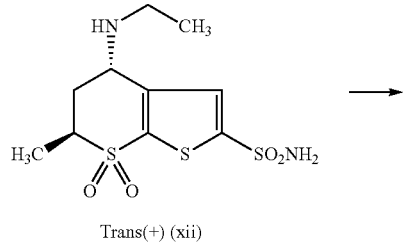

Trans(+) (xii)

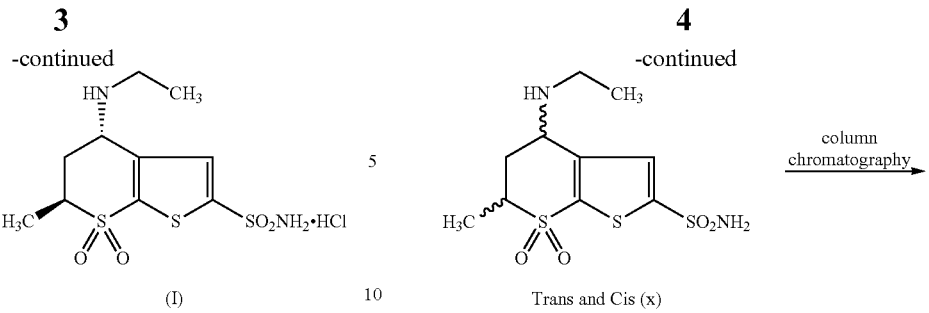

The process disclosed in scheme 1 has following disadvantages.

(a) The reduction of the ketone of sulfonamide (vi) using absolute ethanol is carried out at reflux and then stirred at room temperature for several hours to complete the reaction. This longer duration of reaction produces many impurities.

(b) Oxidation of alcohol (vii) to sulfone (viii) is carried out using oxone. The oxone has many disadvantages such as it is irritating to the eyes, skin, nose and throat. It should be used with adequate ventilation and exposure to its dust should be minimized. Traces of heavy metal salts catalyze the decomposition of oxone. It is practically insoluble in all organic solvents hence a phase transfer catalyst is required.

(c) Activation of the 4-hydroxy group of the sulfoaminated hydroxysulfone (viii) and nucleophilic substitution by desired ethylamine, results in all diastereomeric products (x) i.e. trans and cis isomers, which must be separated by column chromatography and resolved, further using resolving agent. As a result, product loss is greater when the desired product is the more active enantiomer.

An alternate route for the preparation of dorzolamide hydrochloride by the Ritter reaction is disclosed in EP0296879 and consists of the treatment of a aliphatic hydroxyl with a nitrile and a strong acid to form an amide. The process disclosed is as depicted in Scheme 2.

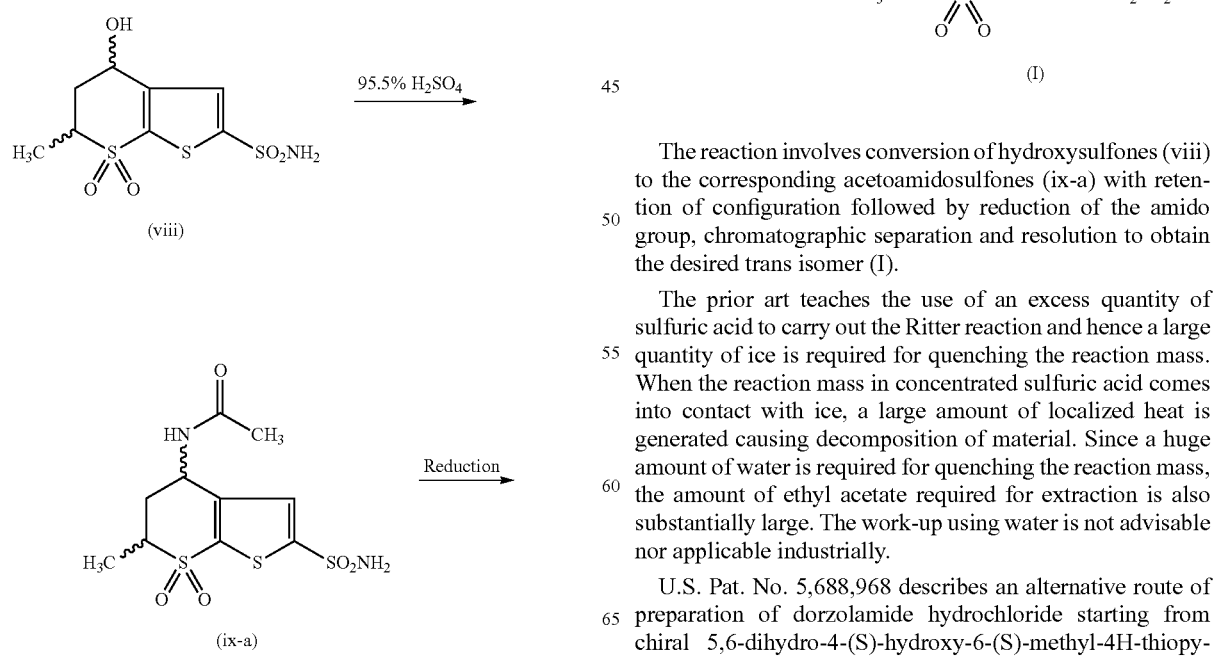

The reaction involves conversion of hydroxysulfones (viii) to the corresponding acetoamidosulfones (ix-a) with retention of configuration followed by reduction of the amido group, chromatographic separation and resolution to obtain the desired trans isomer (I).

The prior art teaches the use of an excess quantity of sulfuric acid to carry out the Ritter reaction and hence a large quantity of ice is required for quenching the reaction mass. When the reaction mass in concentrated sulfuric acid comes into contact with ice, a large amount of localized heat is generated causing decomposition of material. Since a huge amount of water is required for quenching the reaction mass, the amount of ethyl acetate required for extraction is also substantially large. The work-up using water is not advisable nor applicable industrially.

U.S. Pat. No. 5,688,968 describes an alternative route of preparation of dorzolamide hydrochloride starting from chiral 5,6-dihydro-4-(S)-hydroxy-6-(S)-methyl-4H-thiopyran-7,7-dioxide, as depicted in Scheme 3:

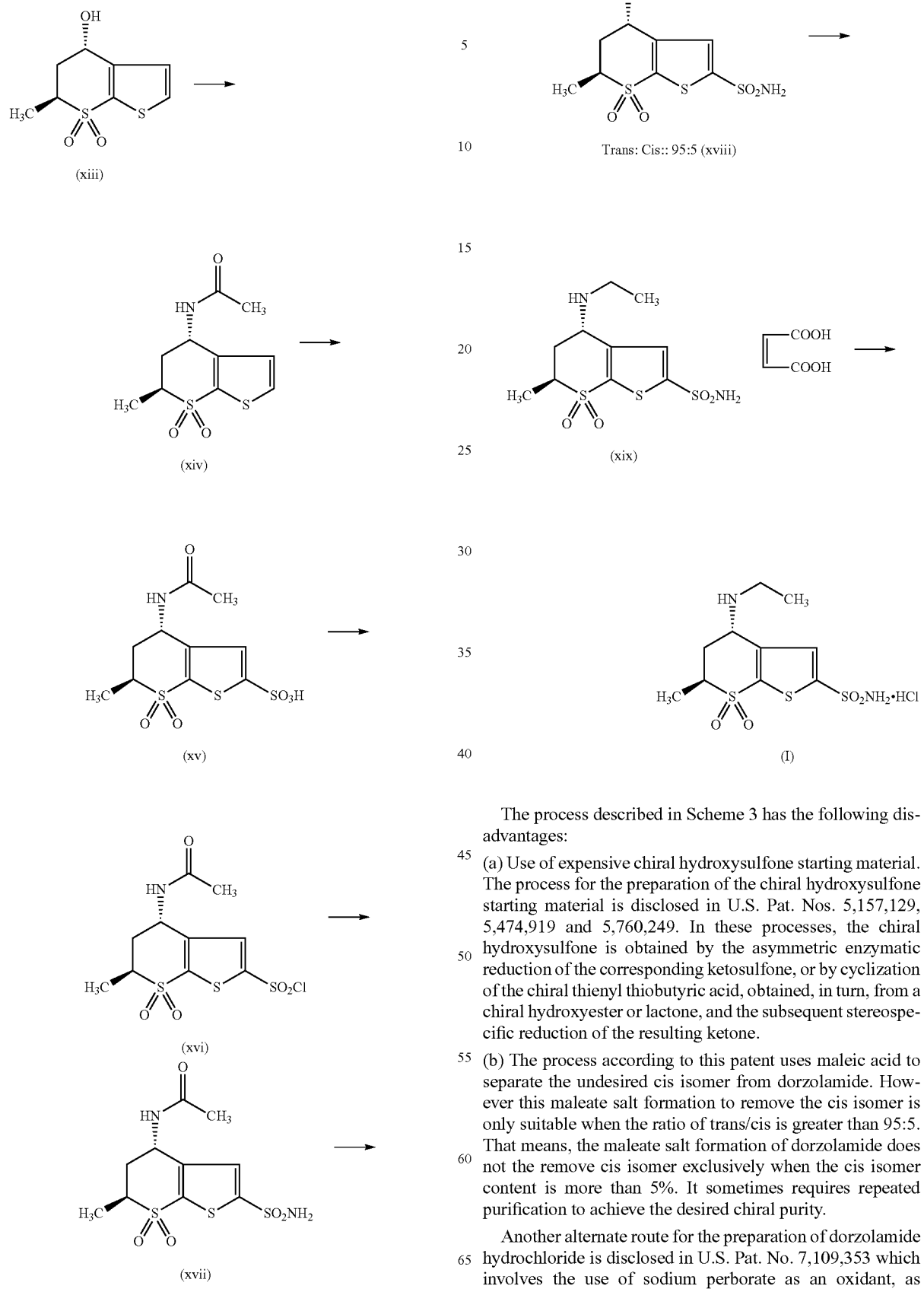

The process described in Scheme 3 has the following disadvantages:

(a) Use of expensive chiral hydroxysulfone starting material. The process for the preparation of the chiral hydroxysulfone starting material is disclosed in U.S. Pat. Nos. 5,157,129, 5,474,919 and 5,760,249. In these processes, the chiral hydroxysulfone is obtained by the asymmetric enzymatic reduction of the corresponding ketosulfone, or by cyclization of the chiral thienyl thiobutyric acid, obtained, in turn, from a chiral hydroxyester or lactone, and the subsequent stereospecific reduction of the resulting ketone.

(b) The process according to this patent uses maleic acid to separate the undesired cis isomer from dorzolamide. However this maleate salt formation to remove the cis isomer is only suitable when the ratio of trans/cis is greater than 95:5. That means, the maleate salt formation of dorzolamide does not the remove cis isomer exclusively when the cis isomer content is more than 5%. It sometimes requires repeated purification to achieve the desired chiral purity.

Another alternate route for the preparation of dorzolamide hydrochloride is disclosed in U.S. Pat. No. 7,109,353 which involves the use of sodium perborate as an oxidant, as depicted in Scheme 4.

Scheme 4

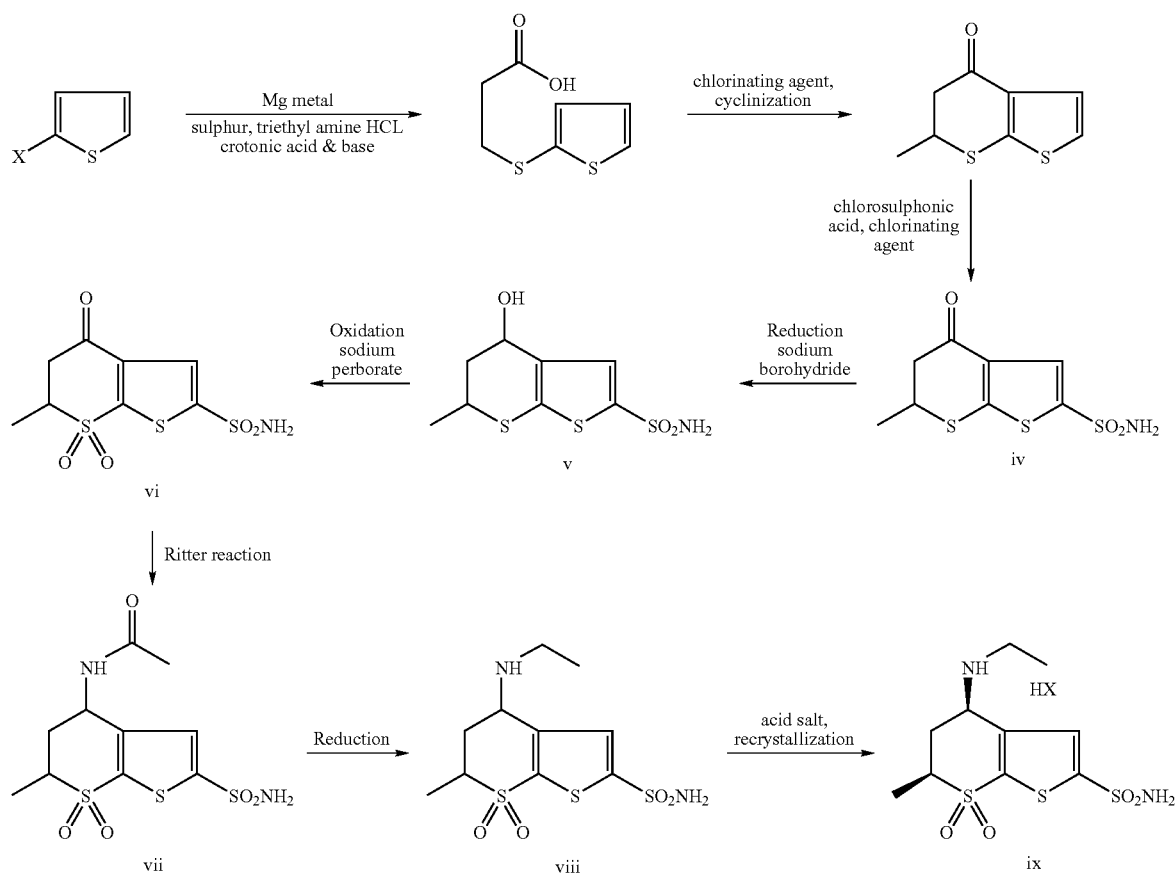

The process disclosed in Scheme 4 has following disadvantages
(a) Conversion of (i) to (ii) requires the mixture to be refluxed for 18-20 hrs which is time consuming and may cause impurity in the product.
(b) As the process uses the Ritter reaction to convert (vi) to (vii), a large amount of water is required to quench the hot mass of reaction which is not practical in an industrial set-up.
(c) Sodium perborate is used as an oxidizing agent to convert (v) to (vi), which has got bleaching properties, and the handling of it may be injurious when done so for a prolonged period.

Yet another process for the preparation of dorzolamide is disclosed in United States publication no. 20060155132 which involves protecting the chiral 5,6-dihydro-4-(R)-hydroxy-6-(S)-methyl-4H-thieno-[2,3-b]thiopyran-7,7-dioxide as depicted in Scheme 5.

Scheme 5

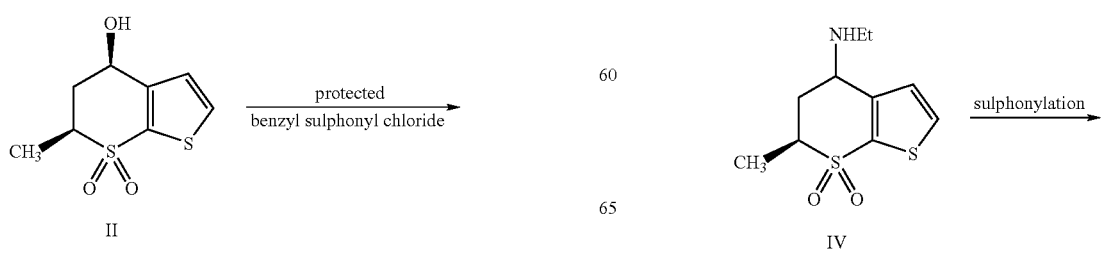

-continued

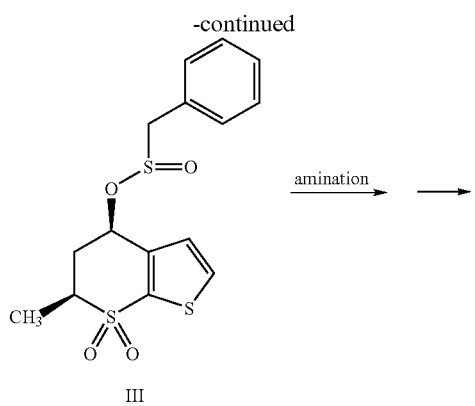

-continued (V)

The process disclosed in Scheme 5 has the following disadvantages.
(a) The conversion process of compound (II) to (III) requires a very low temperature which ranges from −30° to 0° C.
(b) The amination process requires 16-20 hrs, which is time consuming and may cause impurity in the product.

All these disadvantages of the prior art are overcome by the process in accordance with the present invention.

OBJECTIVE OF THE INVENTION

The object of the present invention is to provide a process for commercial manufacture of dorzolamide hydrochloride.

Another object of the present invention is to provide an oxidation process which avoids the use of expensive reagents.

Another object of the present invention is to provide a process which avoids the use of an excessive amount of sulfuric acid and subsequently simplifies work up procedure.

Yet another object of the present invention is to provide a process to separate the cis isomer of dorzolamide.

Yet another object of the present invention is to provide a process which is simple, economical and, suitable for industrial scale-up.

SUMMARY OF THE INVENTION

According to a first aspect of the present invention, there is provided a process for preparing an acetoamido sulfone of formula (viii) comprising oxidation of a hydroxysulfonamide of formula (vii) in the presence of an oxidizing agent.

(vii)

(viii)

In an embodiment, the oxidizing agent is selected from the group consisting of: peracids such as peroxybenzoic acid, m-chloroperbenzoic acid, peracetic acid, peroxytrifluoroacetic acid, peroxysulfuric acid, perboric acid, performic acid, peroxymaleic acid and peroxydichloromaleic acid (for example, prepared from hydrogen peroxide and dichloromaleic anhydride); tert-butyl hydroperoxide optionally in the presence of a vanadium catalyst; dimethyl dioxirane; selenium dioxide; m-phenanthroline di-N-oxide (for example prepared from $H_2O_2$ and m-phenanthroline); nitric acid and hydrogen peroxide. Preferably, the oxidizing agent is hydrogen peroxide.

In an embodiment, the oxidation is catalyzed by tungstic acid or a salt of tungstic acid, such as sodium tungstate. Preferably, the oxidation is catalyzed by sodium tungstate.

A solvent may be used in the oxidation reaction and may be selected from dioxane, tetrahydrofuran, diethyl ether, methanol, tert-butanol, acetic acid, sulfuric acid, water, trifluoroacetic acid, chloroform and mixtures thereof. Preferred solvents for the reaction are water, ethyl acetate or mixtures thereof.

In an embodiment, excess peroxide is present in the reaction mass after reaction completion and this may be decomposed by quenching the reaction mass in a solution of sodium sulphite or manganese dioxide.

The acetoamido sulfone of formula (viii) may be converted to dorzolamide. Any of the prior art processes, for example the EP 0296879 process, for converting the acetoamido sulfone of formula (viii) may be used.

According to another aspect of the present invention, there is provided a process for preparing an acetoamidosulfone of formula (ix-a) comprising converting a hydroxysulfone of formula (viii) to the acetoamidosulfone of formula (ix-a) in the presence of acetonitrile and an acid.

(viii)

(ix-a)

In an embodiment, the acid is sulfuric acid. Suitably, less than 15 molar equivalents of sulfuric acid are used.

Excess sulfuric acid may be present in the reaction mass after reaction completion which may be neutralized by purging with ammonia gas. Ammonium sulfate formed in the neutralization may be separated by filtration.

The acetoamidosulfone of formula (ix-a) may be isolated by concentration of solvent, filtration and quenching with water. In an embodiment, the isolation does not involve sodium bicarbonate washings.

In an embodiment, the hydroxysulfone of formula (viii) is prepared according to the process described above.

The acetoamidosulfone of formula (ix-a) may then be reduced to dorzolamide of formula (x) using a suitable reducing agent as are well known to those skilled in the art.

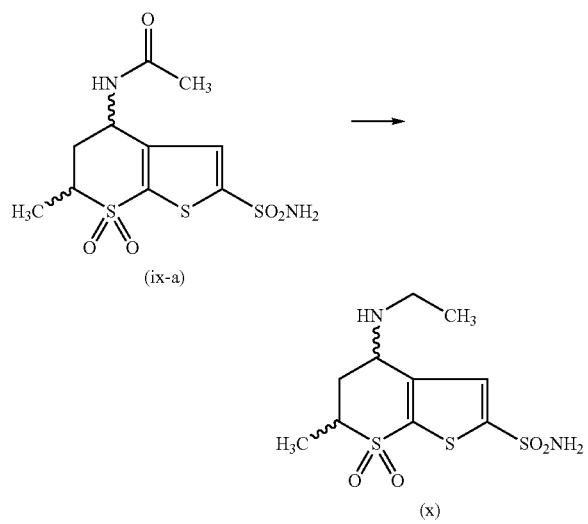

The reducing agent may be NaBH$_4$/BF$_3$(Et$_2$)O.

According to another aspect of the present invention, there is provided a process for separating the cis- and trans-isomers of dorzolamide from a mixture of the trans-isomer of dorzolamide and the cis-isomer of dorzolamide comprising reacting the mixture of isomers with a carboxylic acid.

In an embodiment, the carboxylic acid is selected from the group consisting of fumaric acid, benzoic acid, acetic acid, salicylic acid and p-hydroxybenzoic acid, preferably salicylic acid or p-hydroxy benzoic acid. More preferably, the acid is salicylic acid.

The process of the present invention removes the undesirable cis-isomer from the desired trans-isomer by selectively forming an acid addition salt with the trans-isomer. Thus, the salt of the trans-isomer may be separated from the free base of the cis-isomer. The salicylate salt selectively removes the undesirable cis-isomer from the mixture of isomers of dorzolamide containing up to 30% cis-isomers. Thus, in an embodiment, the mixture of the trans-isomer of dorzolamide and the cis-isomer of dorzolamide contains up to 30% of the cis-isomer of dorzolamide. According to another aspect of the present invention, there is provided dorzolamide salicylate having a trans content of at least 95%, preferably at least 99%. In other words, there is provided a mixture of trans-(±)-dorzolamide salicylate and cis-(±)-dorzolamide in which the percentage of trans-(±)-dorzolamide salicylate is at least 95%, preferably at least 99%. This may also be expressed as trans-(±)-dorzolamide salicylate having a purity of at least 95%, preferably at least 99%.

The reaction with the acid may be carried out in the presence of an organic solvent such as a ketone, ester, alcohol, aliphatic hydrocarbon or aromatic hydrocarbon, or mixtures thereof, preferably in a ketone and an ester and most preferably in ethyl acetate and acetone, either alone or in a mixture.

The trans dorzolamide acid salt may be converted to trans-(±)-dorzolamide base by conventional methods well known to those skilled in the art.

The trans-(±)-dorzolamide base may be resolved using chiral resolving agents such as di-p-toluoyl-tartaric acid. The solvent used is preferably selected from a polar protic or aprotic solvent or a nonpolar solvent or mixtures thereof, preferably a mixture of a polar protic and an aprotic solvent, most preferably a mixture of 2-propanol and acetonitrile. In an embodiment, the solvent is present in about 10 volumes.

The salt of dorzolamide with the resolving agent, for example dorzolamide di-p-toluoyl-L-tartrate salt, may be converted to the hydrochloride salt either by isolating the free base of dorzolamide or without isolation of the free base of dorzolamide.

According to another aspect of the present invention, there is provided trans-(−) dorzolamide hydrochloride having a purity of at least 95%, preferably at least 99%, more preferably at least 99.5%.

According to another aspect of the present invention, there is provided dorzolamide hydrochloride prepared according to a process defined above.

According to another aspect of the present invention, there is provided the use of dorzolamide hydrochloride prepared according to a process defined above in medicine.

According to another aspect of the present invention, there is provided the use of dorzolamide hydrochloride prepared according to a: process defined above in treating ocular hypertension.

The present invention also provides a method of treating a disease state prevented, ameliorated or eliminated by the administration of a carbonic anhydrase inhibitor in a patient in need of such treatment, which method comprises administering to the patient a therapeutically effective amount of dorzolamide hydrochloride prepared according to the present invention, substantially as hereinbefore described.

DETAILED DESCRIPTION OF THE INVENTION

The present invention provides an improved process for the synthesis of dorzolamide hydrochloride of Formula I.

In one aspect, the present invention provides a process for preparing acetoamido sulfones of formula (viii) by oxidation of hydroxysulfonamides of formula (vii) using suitable oxidizing agents, preferably hydrogen peroxide as shown in Scheme 6.

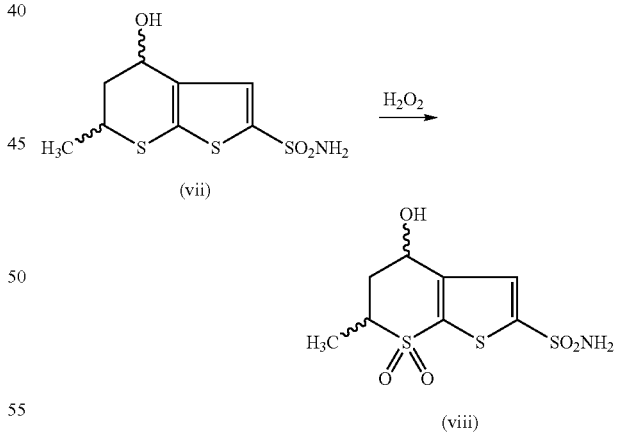

Oxidation of the sulfide to the sulfone in the presence of a solvent using hydrogen peroxide proceeds in good yield, particularly when the reaction is catalyzed by tungstic acid or sodium tungstate, preferably sodium tungstate. Hydrogen peroxide has high active oxygen content and low molecular weight. It is a cheap and widely-available, strong, non-polluting oxidant. Solvents used for the process are selected from dioxane, tetrahydrofuran, diethyl ether, methanol; tert-butanol, acetic acid, sulfuric acid, water, trifluoroacetic acid, chloroform and mixture thereof. Preferred solvents for the reaction are water, ethyl acetate or mixtures thereof. The advantage of these solvents is that, the reaction time is reduced drastically to 2 hours from overnight stirring as reported earlier in the prior art. The excess peroxide may be decomposed by quenching the reaction mass in a solution of sodium sulphite or manganese dioxide, as against evaporation of reaction mass containing oxidant, reported in the prior art. After delivering oxygen, the by-product formed in the hydrogen peroxide oxidation is the nonpolluting water. Hence the use of hydrogen peroxide in the industry is highly favored. Thus, the use of hydrogen peroxide reduces the cost of production, simplifies work-up and minimizes the effluent disposal problem. This forms another aspect of the present invention.

In another aspect, the present invention is directed to an improved process for preparing acetoamidosulfones of formula (ix-a). The reaction may involve conversion of hydroxysulfones of formula (viii) by the Ritter reaction as shown in Scheme 7

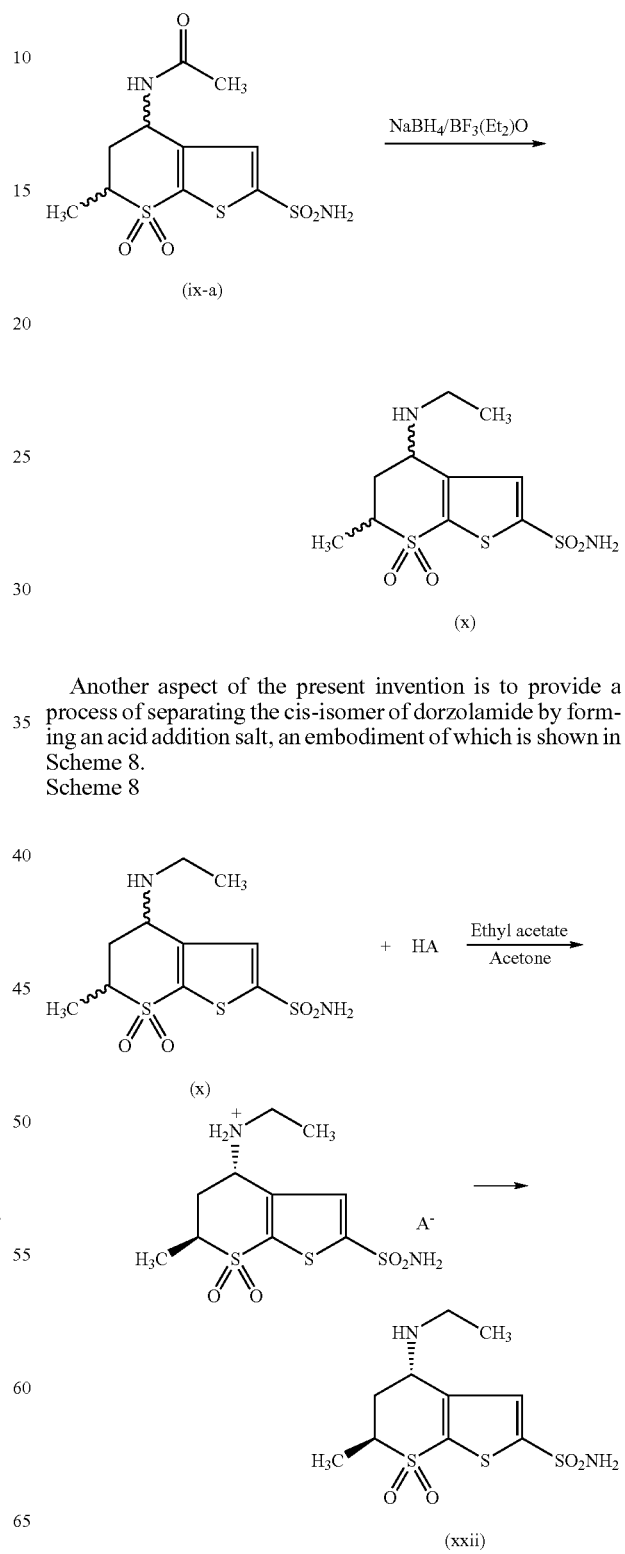

The reaction is carried out in acetonitrile which acts as a solvent and a reactant. Less than molar equivalents of sulfuric acid instead of 19.35 molar equivalents as reported in the prior art may be used, thus avoiding the handling of a large quantity of sulfuric acid. The advantage is that the reaction time is reduced drastically to 6 hours from overnight stirring as reported in the prior art. In the process of the present invention, the work up procedure may be simplified to give the product in high purity and to minimize the formation of impurities which are formed when one employs the work-up procedure given in the prior art. In the present process, after completion of reaction, excess sulfuric acid may be neutralized by purging with ammonia gas. Use of ammonia avoids generation of localized heating, which would otherwise cause decomposition of material by quenching the reaction mass in a large quantity of ice, as reported in the prior art. Ammonium sulfate formed in the reaction may be separated by filtration. The product is easily isolatable by concentrating the organic filtrate to obtain a residue, and quenching the residue in water. The product obtained contains more than 80% of trans-isomers. This process avoids handling a large quantity of solvent such as water and ethyl acetate, and it avoids subsequent sodium bicarbonate washings as reported in the prior art, and this forms another aspect of the present invention.

The acetoamidosulfone of formula (ix-a) may then be reduced to a mixture of cis- and trans-dorzolamide of formula (x) using a suitable reducing agent. The product is obtained with retention of the cis-trans ratio.

Another aspect of the present invention is to provide a process of separating the cis-isomer of dorzolamide by forming an acid addition salt, an embodiment of which is shown in Scheme 8.

Scheme 8 wherein HA is an acid and A⁻ is an anion. The anion corresponds to the acid HA. The acid used in Scheme 8 is preferably a carboxylic acid, or a mineral acid, such as hydrochloric acid, sulfuric acid.

The present invention is also directed to a process for removing the undesirable cis-isomer from the desired trans-isomers by forming an acid addition salt in a solvent or a mixture of solvents, thus avoiding cumbersome column chromatography as reported in the prior art.

The acid used for salt formation may be selected from the group consisting of a carboxylic acid, such as fumaric acid, benzoic acid, acetic acid, salicylic acid, p-hydroxy benzoic acid or benzoic acid, preferably salicylic acid or p-hydroxy benzoic acid. More preferably, the dorzolamide salt is trans (±)-dorzolamide salicylate. The salicylate salt selectively removes the undesirable cis-isomer from the dorzolamide containing up to 30% cis isomers as against other acid addition salts which are capable of removing cis-isomer when the content of undesired cis isomers in the dorzolamide is not more than 5% as reported in the prior art. The salt preparation may be carried out in the presence of organic solvents such as a ketone, ester, alcohol, aliphatic hydrocarbon or aromatic hydrocarbon, or mixtures thereof, preferably in ketone and an ester and most preferably in ethyl acetate and acetone, either alone or in combination thereof. The dorzolamide salicylate thus obtained contains trans-(±)-dorzolamide having a percentage of cis-isomer below 1%.

The trans dorzolamide salicylate thus formed may be converted to trans-(±)-dorzolamide base of formula (xii) by conventional methods.

The trans-(±)-dorzolamide base of formula (xii) may then be resolved using chiral resolving agents such as, di-p-toluoyl-tartaric acid. The solvent used is preferably selected from polar protic or aprotic solvents or nonpolar solvents or mixtures thereof, preferably mixtures of polar protic and aprotic solvents, most preferably a mixture of 2-propanol and acetonitrile. This combination of solvents is advantageous over solvents used in the prior art such as n-propanol which require about 100 volumes when used alone to resolve the trans isomer. In the present process, the desired trans (−) isomer may be easily isolated by using about 10 volumes of solvent, thus reducing the reaction volume and time, and increasing batch size and yield, and this forms another aspect of the present invention.

The salt of dorzolamide and resolving agent, for example dorzolamide di-p-toluoyl-L-tartrate salt, may be converted to the hydrochloride salt either by isolating the base or without isolation of the base. The dorzolamide hydrochloride prepared by this method does not contain more than 0.5% of the corresponding 4R,6R diastereomer.

The following non-limiting examples illustrate the processes provided by the present invention without limiting its scope.

EXAMPLE 1

Preparation of 5,6-Dihydro-4H-4-hydroxy-6-methylthieno[2,3-b]thiopyran-2-sulfonamide To a suspension of 5,6-dihydro-4H-6-methylthio[2,3-b] thiopyran-4-one-2-sulfonamide (100.0 gms, 0.54 moles) in methanol was added, sodium borohydride (20.0 gms, 0.52 moles) at 0° C. to 5° C. The mixture was stirred at 0° C. to 5° C. for 15 minutes and then at 25° C. to 30° C. for 2 hours. Methanol was distilled out from the reaction mass under vacuum below 50° C. The reaction mass was cooled to 25° C. to 30° C. and charged with 1000 ml water. Reaction mass was further cooled to 10° C., acidified to pH 2 with sulphuric acid (29.9 gms, 0.30 moles) and stirred for 15 minutes. The pH of the reaction mass was adjusted to 7-8 using 10% sodium hydroxide solution maintaining temperature below 10° C. The reaction mass was stirred for 15 minutes at 10° C. and then at 25° C. to 30° C. for 10 minutes. The product was extracted in 1000 ml. Ethyl Acetate thrice. The solvent was evaporated under reduced pressure to give 100.7 gms of the title compound.

EXAMPLE 2

Preparation of 5,6-Dihydro-4H-4-hydroxy-6-methylthieno[2,3-b]thiopyran-2-sulfonamide-7,7-dioxide To a solution of 5,6-dihydro-4H-4-hydroxy-6-methylthieno[2,3-b]thiopyran-2-sulfonamide (100.7 gms, 0.37 moles) in 900 ml ethyl acetate and 100 ml water was added sodium tungstate (12.75 gms, 0.038 moles) at 25° C. to 30° C. The reaction mass was cooled to 5° C. A solution of 30% $H_2O_2$ (200.0 ml, i.e. 222 gms, 1.95 moles) was added slowly to the reaction mass by maintaining temperature below 5° C. and was stirred further at 0° C. to 10° C. for 1 hour. The temperature was raised to 25° C. to 30° C. and stirred for 1 hour. Added 10% sodium sulphite solution (100 gms, 0.79 moles in 1000 ml water) between 0° C. to 5° C. Reaction mass was stirred at 25° C. to 30° C. for 15 minutes. The layers were separated and aqueous layer was washed four times with 500 ml ethyl acetate. The combined organic layers were washed with 10% sodium chloride solution and dried over sodium sulphate. The solvent was distilled under reduced pressure up to 2 volumes and was cooled to 25° C. to 30° C., stirred for 1 hour and isolated by filtration to get title compound (92.5 gms).

EXAMPLE 3

Preparation of 5,6-Dihydro-4H-4-acetylamino-6-methylthieno[2,3-b]thiopyran-2-sulfonamide-7,7-dioxide To 5,6-dihydro-4H-4-hydroxy-6-methylthieno[2,3-b]thiopyran-2-sulfonamide-7,7-dioxide (92.5 gms, 0.31 moles) in acetonitrile (1110 ml) was added sulphuric acid 98% (165.7 ml, 205 gms, 3.11 moles) dropwise below 5° C. After the addition, the suspension was allowed to warm to 25° C. and stirred for 6 hours. The pH of the reaction mass was adjusted to 9-10 using ammonia gas between 10° C. to 20° C. The reaction mass was further stirred at 25° C. for 1 hour, filtered and washed with 500 ml acetonitrile. Solvent was distilled under reduced pressure to obtain residue. The solvent traces were removed by water; under vacuum at 70° C. to 80° C. The residue was cooled to 25° C. to 30° C., stirred and filtered to get of 5,6-Dihydro-4H-4-acetylamino-6-methylthieno[2,3-b]thiopyran-2-sulfonamide-7,7-dioxide (83.25 gms).

EXAMPLE 4

Preparation of 5,6-Dihydro-4H-4-ethylamino-6-methylthieno[2,3-b]thiopyran-2-sulfonamide-7,7-dioxide A suspension of 5,6-dihydro-4H-4-acetylamino-6-methylthieno[2,3-b]thiopyran-2-sulfonamide-7,7-dioxide (83.25 gms, 0.24 moles) in THF (832 ml) was cooled to 0° C. and sodium borohydride (49.11 gms, 1.29 moles) was added in lots maintaining temperature below 5° C. Reaction mass was stirred for 15 minutes at 5° C. and boron trifluoride diethyletherate (249.75 ml, 287.2 gms, 2.02 moles) was added below 5° C. The reaction mass was stirred for 5 hours at 0° C. to 5° C. Temperature of the reaction mass was raised to 25° C. to 30° C. and stirred for 18 hours. The reaction mass was quenched in 1M sulphuric acid solution (1082 ml) below 5° C., temperature raised to 25° C. to 30° C. and stirred for 1 hour. The solvent was distilled under reduced pressure at 80° C. The reaction mass was cooled to 10° C. and pH adjusted to 7-8 using 50% sodium hydroxide solution. Material was extracted in 1665 ml ethyl acetate once and 832 ml twice. The combined organic layers were washed with saturated sodium chloride solution, dried over sodium sulphate, charcoalised, filtered on hyflo, distilled to get title compound (77.42 gms).
HPLC: 80:20::Trans:Cis

EXAMPLE 5

(a) Preparation of 5,6-Dihydro-4H-4-ethylamino-6-methylthieno[2,3-b]thiopyran-2-sulfonamide-7,7-dioxide salicylate To ethyl acetate (541.9 ml) and acetone (309.68 ml) was added, the product from example 4 (77.42 gms, 0.23 moles, 80% trans). The reaction mass was heated at 45-50° C. to get clear solution and salicylic acid (37.92 gms, 0.27 moles) was added at 45° C. to 50° C. Reaction mass was refluxed for 1 hour and cooled to 25° C. to 30° C. and stirred for 2 hours. Solid obtained was isolated by filtration. The filtered cake was purified in a solvent mixture of ethyl acetate:acetone (5:3 volumes) to obtain 68.10 gms of salicylate salt.
Trans isomer>99.9%
Cis isomer<0.1%

Thus, the content of the trans isomer is enriched from 80% to over 99%.

(b) Preparation of 5,6-Dihydro-4H-4-ethylamino-6-methylthieno[2,3-b]thiopyran-2-sulfonamide-7,7-dioxide p-hydroxy benzoate 5,6-dihydro-4H-4-ethylamino-6-methylthieno[2,3-b]thiopyran-2-sulfonamide-7,7-dioxide p-hydroxy benzoate was obtained in a similar manner in 70% yield from 5,6-dihydro-4H-4-ethylamino-6-methylthieno[2,3-b]thiopyran-2-sulfonamide-7,7-dioxide and p-hydroxy benzoic acid.

(c) Preparation of 5,6-dihydro-4H-4-ethylamino-6-methylthieno[2,3-b]thiopyran-2-sulfonamide-7,7-dioxide benzoate 5,6-dihydro-4H-4-ethylamino-6-methylthieno[2,3-b]thiopyran-2-sulfonamide-7,7-dioxide benzoate was obtained in a similar way in 76% yield from 5,6-dihydro-4H-4-ethylamino-6-methylthieno[2,3-b]thiopyran-2-sulfonamide-7,7-dioxide and benzoic acid.

EXAMPLE 6

5,6-Dihydro-4H-4-ethylamino-6-methylthieno[2,3-b]thiopyran-2-sulfonamide-7,7-dioxide di-p-toluoyl-(L) tartrate (a) The salicylate salt prepared in example 5(a) (68.1 gms, 0.14 moles) was taken in ethyl acetate (955.0 ml), and basified with saturated sodium bicarbonate solution (284.0 ml). The reaction mass stirred for 15 minutes at 25° C. to 30° C. and aqueous layer was extracted with ethyl acetate (476 ml×2) and organic layers were combined, washed with brine solution and dried over sodium sulphate. The clear solvent solution was removed completely by distillation. The residue was dissolved in mixture of isopropanol:acetonitrile (2:1) 476 ml to get clear solution, di-p-toluoyl-L-tartarate (62.4 gms) was added at reflux and refluxed for 1 hour. The reaction mass was cooled to 25° C. and stirred for 2 hours. Product was isolated by filtration and recrystallized in isopropanol:acetonitrile (500 ml) to yield 44.26 gms of title compound.
Trans (−) dorzolamide di-p-toluoyl-L-tartrate>99.5%
Trans (+) dorzolamide di-p-toluoyl-D-tartrate<0.5%
Cis Isomer<0.1%

(b) Similarly, using the procedure described in Example 6(a), the title compound was obtained from the p-hydroxy benzoate salt of example 5(b).

(c) Similarly, using the procedure described in Example 6(a), the title compound was obtained from the benzoate salt of example 5(c).

EXAMPLE 7

Preparation of 5,6-Dihydro-4H-4-ethylamino-6-methylthieno[2,3-b]thiopyran-2-sulfonamide-7,7-dioxide hydrochloride (a) Dorzolamide di-p-toluoyl-L-tartrate salt as prepared in example 6 (44.26 gms, 0.085 moles) was taken in ethyl acetate (557.0 ml), basified with saturated sodium bicarbonate solution. Reaction mass was stirred for 15 minutes at 25° C. to 30° C. and aqueous layer was extracted with ethyl acetate (278 ml×2). The organic layers were combined, washed with brine solution, dried over sodium sulphate, and charcoalized. To the clear solution, IPA+HCL (16.35 ml, 0.089 moles) was added, stirred for 30 minutes and ethyl acetate was removed by distillation at atmospheric pressure at 85° C. to about 280 ml volume, cooled to 25-30° C., stirred for 12 hours at same temperature and filtered to get 26.0 gms of dorzolamide hydrochloride.
Trans (−) dorzolamide hydrochloride>99.5%
Trans (+) dorzolamide hydrochloride<0.5%
Cis Isomer<0.1%

(b) Dorzolamide hydrochloride was obtained in a similar manner in quantitative yield from the salt of example 6(b).

(c) Dorzolamide hydrochloride was obtained in a similar manner in quantitative yield from the salt of example 6(c).

EXAMPLE 8

Preparation of 5,6-Dihydro-4H-4-ethylamino-6-methylthieno[2,3-b]thiopyran-2-sulfonamide-7,7-dioxide hydrochloride without isolation of base Dorzolamide di-p-toluoyl-L-tartrate (50 gms, 0.096 moles) prepared as per example 6, was charged in a round bottom flask along with isopropanol (1000 ml). The reaction mass was heated to 80° C. and charged with IPA-HCl (20 ml) dropwise to pH 3 to 4. The reaction mass was heated to reflux for 5-10 minutes. The clear solution obtained was concentrated to 100 ml. The reaction mass was charged with 300 ml ethyl acetate, cooled to 25° C., stirred for 12 to 14 hours at same temperature. The resulting dorzolamide hydrochloride was isolated by filtration and washed with ethyl acetate (50 ml), dried under vacuum at 60-65° C. for 5-6 hours. Yield-30 gms.
Trans (−) dorzolamide hydrochloride>99.5%
Trans (+) dorzolamide hydrochloride<0.5%
Cis Isomer<0.1%

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the examples are therefore intended to be embraced therein.

The invention claimed is:

1. A process for preparing an acetoamido sulfone of formula (viii) comprising oxidation of a hydroxysulfonamide of formula (vii) in the presence of an oxidizing agent selected from the group consisting of: a peracid, tert-butyl hydroperoxide, dimethyl dioxirane, selenium dioxide, m-phenanthroline di-N-oxide, nitric acid and hydrogen peroxide

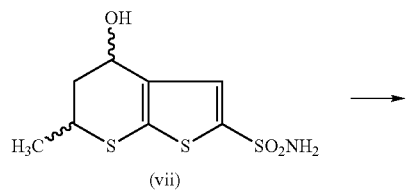

2. The process according to claim 1, wherein the oxidizing agent is selected from the group consisting of: hydrogen peroxide, peroxybenzoic acid, m-chloroperbenzoic acid, peracetic acid, peroxytrifluoroacetic acid, peroxysulfuric acid, perboric acid, performic acid, peroxymaleic acid and peroxydichloromaleic acid.

3. The process according to claim 1, wherein the oxidation is catalyzed by tungstic acid or a salt of tungstic acid.

4. The process according to claim 1, wherein the oxidation is carried out in the presence of a solvent selected from the group consisting of ethyl acetate, dioxane, tetrahydrofuran, diethyl ether, methanol, tert-butanol, acetic acid, sulfuric acid, water, trifluoroacetic acid, chloroform and mixtures thereof.

5. The process according to claim 1, wherein excess peroxide is present in the reaction mass after completion of the oxidation, which excess is decomposed by quenching the reaction mass in a solution of sodium sulphite or manganese dioxide.

6. The process for preparing an acetoamidosulfone of formula (ix-a) comprising preparing a hydroxysulfone of formula (viii) according to claim 1 and converting the hydroxysulfone of formula (viii) to the acetoamidosulfone of formula (ix-a) in the presence of acetonitrile and an acid

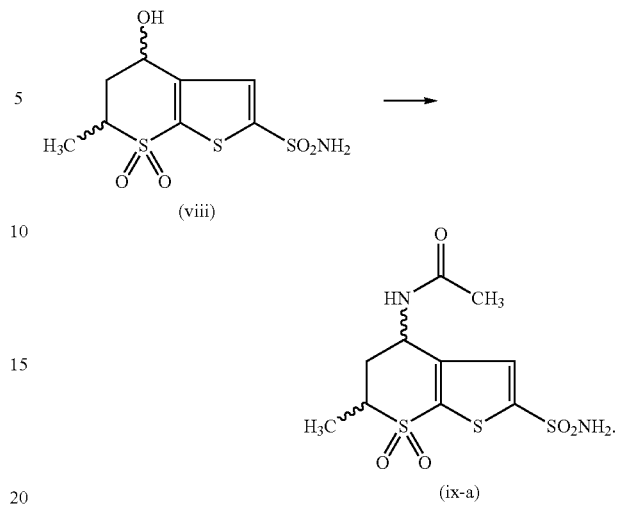

7. The process according to claim 6, wherein excess sulfuric acid is present in the reaction mass after completion of the conversion reaction, which excess is neutralized by purging with ammonia gas.

8. The process for preparing dorzolamide of formula (x) comprising preparing an acetoamidosulfone of formula (ix-a) according to claim 6, followed by reducing the acetoamidosulfone of formula (ix-a) using a suitable reducing agent

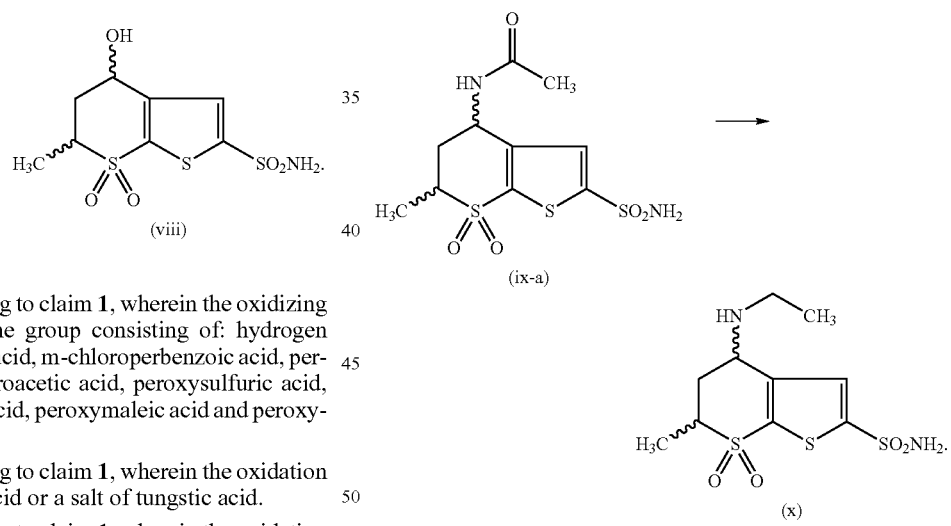

9. A process for separating the cis and trans isomers of dorzolamide from a mixture of the trans isomer of dorzolamide and the cis isomer of dorzolamide, the process comprising preparing dorzolamide according to claim 8, wherein the dorzolamide is in the form of a mixture of cis and trans isomers, and reacting the mixture of isomers with a carboxylic acid.

10. The process according to claim 9, wherein the carboxylic acid is selected from the group consisting of fumaric acid, benzoic acid, acetic acid, salicylic acid and p-hydroxybenzoic acid.

11. The process according to claim 10, wherein the carboxylic acid is salicylic acid and, following reaction with salicylic acid, the content of the trans isomer in the reaction mixture is at least 99%.

12. The process according to claim 9, wherein the reaction with the carboxylic acid is carried out in the presence of an organic solvent selected from a group consisting of a ketone, ester, alcohol, aliphatic hydrocarbon or aromatic hydrocarbon, and mixtures thereof.

13. The process according to claim 9, wherein the trans dorzolamide acid salt is converted to trans-(±)-dorzolamide base.

14. The process according to claim 13, wherein the trans-(±)-dorzolamide base is resolved in the presence of a chiral resolving agent.

15. The process according to claim 14, wherein the salt of dorzolamide is converted to the hydrochloride salt of dorzolamide.

16. The process according to claim 1, wherein the oxidizing agent comprises hydrogen peroxide.

17. The process according to claim 1, wherein the oxidation is catalyzed by sodium tungstate.

18. The process according to claim 1, wherein the oxidation is carried out in the presence of a solvent selected from the group consisting of water, ethyl acetate, and mixtures thereof.

19. The process for preparing an acetoamidosulfone of formula (ix-a) comprising preparing a hydroxysulfone of formula (viii) according to claim 1 and converting the hydroxysulfone of formula (viii) to the acetoamidosulfone of formula (ix-a) in the presence of acetonitrile and sulfuric acid.

20. The process for preparing dorzolamide of formula (x) comprising preparing an acetoamidosulfone of formula (ix-a) according to claim 6, followed by reducing the acetoamidosulfone of formula (ix-a) using $NaBH_4/BF_3(Et_2)O$

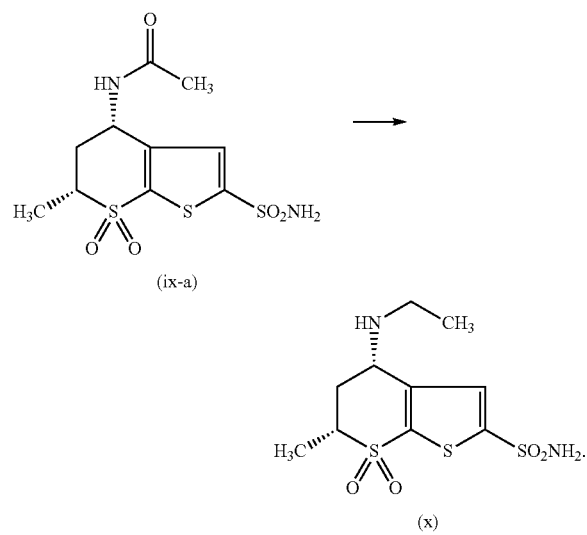

21. The process according to claim 9, wherein the carboxylic acid is selected from the group consisting of salicylic acid, p-hydroxy benzoic acid, and mixtures thereof.

22. The process according to claim 9, wherein the carboxylic acid comprises salicylic acid.

23. The process according to claim 13, wherein the trans-(±)-dorzolamide base is resolved in the presence of di-p-toluoyl-tartaric acid.

* * * * *

UNITED STATES PATENT AND TRADEMARK OFFICE
CERTIFICATE OF CORRECTION

PATENT NO. : 8,263,787 B2
APPLICATION NO. : 12/598557
DATED : September 11, 2012
INVENTOR(S) : Rajendra Narayanrao Kankan et al.

It is certified that error appears in the above-identified patent and that said Letters Patent is hereby corrected as shown below:

Column 19, Lines 58-62, delete "5. The process according to claim 1, wherein excess peroxide is present in the reaction mass after completion of the oxidation, which excess is decomposed by quenching the reaction mass in a solution of sodium sulphite or manganese dioxide."

Signed and Sealed this
Eighteenth Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,263,787 B2
APPLICATION NO. : 12/598557
DATED : September 11, 2012
INVENTOR(S) : Rajendra Narayanrao Kankan et al.

It is certified that error appears in the above-identified patent and that said Letters Patent is hereby corrected as shown below:

Delete the title page and substitute therefore the attached title page showing the corrected number of claims in patent.

Column 19, Lines 58-62, delete "5. The process according to claim 1, wherein excess peroxide is present in the reaction mass after completion of the oxidation, which excess is decomposed by quenching the reaction mass in a solution of sodium sulphite or manganese dioxide."

This certificate supersedes the Certificate of Correction issued December 18, 2012.

Signed and Sealed this
Twenty-sixth Day of February, 2013

Teresa Stanek Rea
*Acting Director of the United States Patent and Trademark Office*

United States Patent
Kankan et al.

(10) Patent No.: US 8,263,787 B2
(45) Date of Patent: Sep. 11, 2012

(54) PROCESS FOR PREPARING DORZOLAMIDE

(75) Inventors: Rajendra Narayanrao Kankan, Maharashtra (IN); Dharmaraj Ramachandra Rao, Maharashtra (IN); Shrikant Suresh Mudgal, Maharashtra (IN)

(73) Assignee: CIPLA Limited, Mumbai (IN)

( * ) Notice: Subject to any disclaimer, the term of this patent is extended or adjusted under 35 U.S.C. 154(b) by 310 days.

(21) Appl. No.: 12/598,557

(22) PCT Filed: May 7, 2008

(86) PCT No.: PCT/GB2008/001592
§ 371 (c)(1),
(2), (4) Date: Dec. 30, 2009

(87) PCT Pub. No.: WO2008/135770
PCT Pub. Date: Nov. 13, 2008

(65) Prior Publication Data
US 2010/0113804 A1  May 6, 2010

(30) Foreign Application Priority Data
May 7, 2007  (IN) .................................. 866/07

(51) Int. Cl.
*C07D 409/02*  (2006.01)
(52) U.S. Cl. ........................................ 549/23
(58) Field of Classification Search ............ 549/23
See application file for complete search history.

(56) References Cited

U.S. PATENT DOCUMENTS

| | | |
|---|---|---|
| 5,157,129 A | 10/1992 | Blacklock et al. |
| 5,474,919 A | 12/1995 | Chartrain et al. |
| 5,688,968 A | 11/1997 | Blacklock et al. |
| 5,760,249 A | 6/1998 | Mathre et al. |
| 7,109,353 B2 | 9/2006 | Gurjar et al. |
| 2006/0155132 A1 | 7/2006 | Kovacs et al. |

FOREIGN PATENT DOCUMENTS

| | | |
|---|---|---|
| EP | 0296879 A1 | 12/1988 |
| WO | 9421645 A1 | 9/1994 |
| WO | 2008135770 A2 | 11/2008 |
| WO | 2008135770 A3 | 11/2008 |

OTHER PUBLICATIONS

Grant, Ed., Hackh's Chemical Dictionary, 4th edition.*
Foreign communication from the priority application—International Search Report and Written Opinion, PCT/GB2008/001592, Mar. 27, 2009, 20 pages.
Foreign communication from the priority application—International Preliminary Report on Patentability, PCT/GB2008/001592, Nov. 19, 2009, 11 pages.

* cited by examiner

*Primary Examiner* — Taofiq A Solola
(74) *Attorney, Agent, or Firm* — Conley Rose, P.C.; Rodney B. Carroll

(57) ABSTRACT

There is provided a process for preparing dorzolamide and processes for preparing intermediates useful in the preparation of dorzolamide. In particular, there is provided a process for preparing an acetoamido sulfone of formula (viii) comprising oxidation of a hydroxysulfonamide of formula (vii) in the presence of an oxidizing agent selected from the group consisting of: a peracid, tert-butyl hydroperoxide, dimethyl dioxirane, selenium dioxide, m-phenanthroline di-N-oxide, nitric acid and hydrogen peroxide. There is also provided a process for preparing an acetoamidosulfone of formula (ix-a) comprising converting a hydroxysulfone of formula (viii) to the acetoamidosulfone of formula (ix-a) in the presence of acetonitrile and an acid. There is also provided a process for separating the cis- and trans-isomers of dorzolamide from a mixture of the trans-isomer of dorzolamide and the cis-isomer of dorzolamide comprising reacting the mixture of isomers with a carboxylic acid.

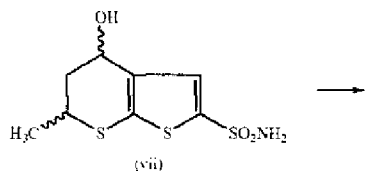

(vii)

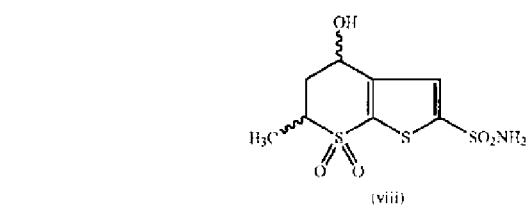

(viii)

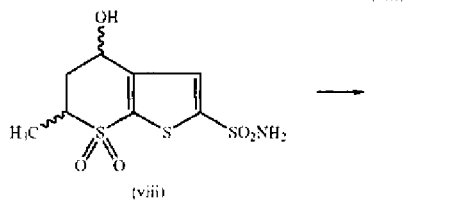

(ix-a)

22 Claims, No Drawings

UNITED STATES PATENT AND TRADEMARK OFFICE
CERTIFICATE OF CORRECTION

PATENT NO. : 8,263,787 B2  
APPLICATION NO. : 12/598557  
DATED : September 11, 2012  
INVENTOR(S) : Rajendra Narayanrao Kankan Page 1 of 1

It is certified that error appears in the above-identified patent and that said Letters Patent is hereby corrected as shown below:

Title Page, Line 4 of the Abstract, Item (57), replace "an acetoamido sulfone" with --a hydroxysulfone--

In the Specification

Column 9, Line 39: replace "an acetoamido sulfone" with --a hydroxysulfone--

Column 10, Line 20: replace "acetoamido sulfone" with --hydroxysulfone--

Column 10, Lines 22-23: replace "acetoamido sulfone" with --hydroxysulfone--

Column 12, Line 33: replace "acetoamido sulfone" with --hydroxysulfone--

In the Claims

Column 19, Line 11: replace "an acetoamido sulfone" with --a hydroxysulfone--

Signed and Sealed this  
Twelfth Day of November, 2013

Teresa Stanek Rea  
*Deputy Director of the United States Patent and Trademark Office*